United States Patent [19]

Zorgniotti

[11] Patent Number: 4,957,104
[45] Date of Patent: Sep. 18, 1990

[54] IMPROVEMENTS TO OBVIATE PURE VENOUS IMPOTENCE

[76] Inventor: Adrian W. Zorgniotti, 33 E. 74th St., New York, N.Y. 10021

[21] Appl. No.: 343,628

[22] Filed: Apr. 27, 1989

[51] Int. Cl.⁵ ............................................. A61F 2/26
[52] U.S. Cl. ...................................................... 128/79
[58] Field of Search ........................... 128/79, 325, 327

[56] References Cited

U.S. PATENT DOCUMENTS 4,531,519  7/1985  Dunn et al. ........................... 128/325
4,532,920  8/1985  Finney ..................................... 128/79
4,829,990  5/1989  Thuroff et al. ....................... 128/327

Primary Examiner—Cary E. Stone
Attorney, Agent, or Firm—Myron Amer

[57] ABSTRACT

A method of diminishing venous leakage to obviate male impotence by injecting fluid into penis implants so as to increase the size of these implants and correspondingly squeeze the flow passage of the leakage that is between the implants to reduce flow through the squeezed flow passage.

4 Claims, 2 Drawing Sheets

IMPROVEMENTS TO OBVIATE PURE VENOUS IMPOTENCE

The present invention relates generally to improvements for obviating male impotence of the type attributable to "venous leakage", and more particularly to an invaginable implant device to aid in the implementation and maintenance of an erection by restricting the outflowing blood constituting said "venous leakage".

As already well known, a penis erection is a complex reflex action initiated by physical and mental sexual stimulation causing in the main artery system of the penis an increase of blood to enter the penis and, for the duration of the erection there is a delicate balance of blood flow into and out of the penis, controlled by "valves" within and muscles surrounding arteries and veins, providing the necessary differential blood pressure to maintain the erection.

In a patient suffering from what is known as pure venous impotence, there is difficulty in resticting the outflow of blood from the penis, which is classified as "venous leakage". Depending on the degree of disability, the patient is able to achieve an erection of only a short duration, or none at all.

EXAMPLE OF PRIOR ART

It is already well known, as exemplified by the efforts of doctors M. Degni and R. E. Tullii and described in their article published for the Internaitonal Society For Impotence Research for a meeting in Boston, Mass. on Oct. 6–9, 1988, entitled "The Results Of A New Surgical Technique In 60 Patients With Pure Venous Impotence", that an implant surgically located in the penis venous outflowing system will, as a function of space occupied by the implant, squeeze closed the network of veins of the system and, in this way, restrict the existing blood and correct the venous leakage.

A significant shortcoming of the noted procedure is that the extent of the venous system that should be closed is not readily determinable by preliminary testing or otherwise, and thus often must be arrived at in multiple surgical procedures. If a greater extent of the venous system is closed, there is an adverse consequence to the patient, and thus some of the implant must be removed. On the other extreme, if the extent of the venous system that is squeezed closed does not obviate the venous leakage necessary to maintain an erection, the patient must undergo additional surgery to receive an additional implant.

Overcoming the aforesaid and other shortcomings of the prior art, the within inventive method contemplates the use of an implant that post-surgically, and in a simple, readily performed transcutaneous hypodermic procedure, can be varied in size to correspondingly vary the extent of the venous system that is squeezed closed, thus providing a precise control over the existing blood flow and is thus effective to correct the venous leakage disability with minimum inconvenience and trauma to the patient.

The description of the invention which follows, together with the accompanying drawings should not be construed as limiting the invention to the example shown and described, because those skilled in the art to which this invention appertains will be able to devise other forms thereof within the ambit of the appended claims.

As a preliminary to a detailed discription of the drawings, it is helpful to note that the within invention defines a method of obviating male impotence of a specific type, namely that commonly referred to as "venous leakage", and that, more particularly, although surgical procedures are already known to cure this problem, these known surgical procedures are not as effective as that of the within invention. Thus, the inventive method is a surgical procedure to obviate male impotence due to venous leakage which is significantly more effective that known surgical procedures directed to the same problem.

Figure 1:
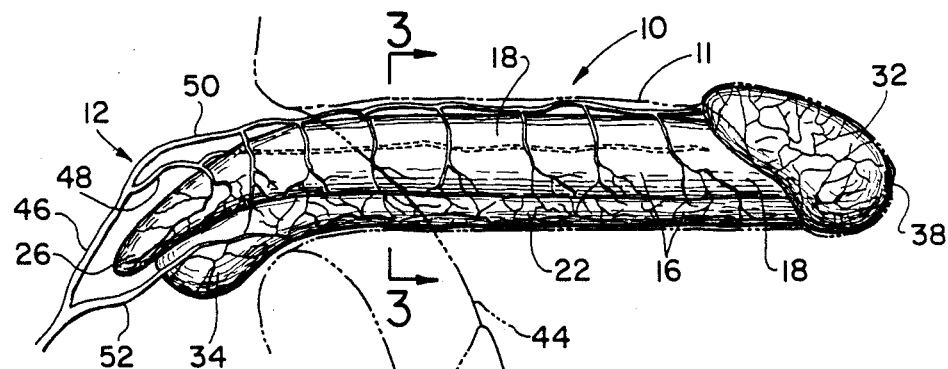
FIG. 1 is a side elevation of an erect penis providing disclosure of pertinent components and parts of the arterial system thereof.

Although the inventive method and the anatomy of the penis necessary for understanding the method will be described in greater detail subsequently, it is helpful to note general aspects of FIGS. 1, 4, 5 and 6. In FIG. 1, penis 10 is shown in a flaccid condition, as noted by the triple dot reference line 44, and in full line as an erection which is the known condition preliminary to ejaculation, involving a complex interplay of brain, nerves, glands, muscles and blood vessels that combine as a reflex action initiated by physical and mental sexual stimulation. Most significant to the achieving of the erection are changes within the main artery system 12 which allow for an increase of blood to enter the three cylinders 16 of penis 10 (See FIG. 4) through its many branches. For the duration of the erection there is a delicate balance of blood flow into and out of the penis 10 controlled by valves within and muscles surrounding arteries 12 and veins 14, resulting in the necessary differential blood pressure to maintain the erection.

In the case of pure venous impotence, the patient is found to have a difficulty in his ability to restrict the outflow of blood from the penis, which is classified as "venous leakage". Depending on the degree of disability, the patient is able to achieve an erection of short duration, or none at all.

Figure 5:
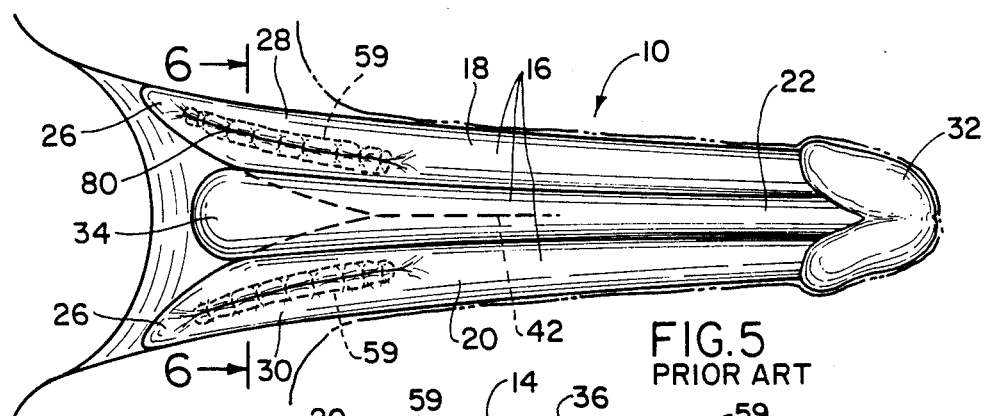
FIG. 5 is a bottom view similar to FIG. 4, but illustrating a current surgical procedure for comparison to the within inventive procedure.
Figure 6:
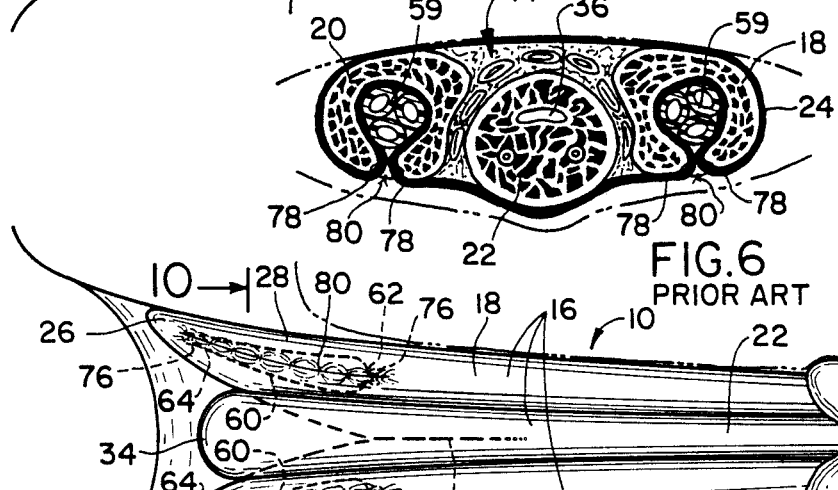
FIG. 6 is a cross section taken along line 6—6 of FIG. 5.

The known surgical procedure for obviating male impotence due to venous leakage will be subsequently described in general terms in connection with FIGS. 5 and 6. It consists, in its general approach, in suturing an implant of a fixed shape to take up a volume corresponding to said shape in the penis outflowing blood venous system and in this way squeeze closed a portion of the venous system and restrict outflowing blood. A significant shortcoming to be noted in this currently used surgical procedure is that the extent of the venous system that should be closed is not readily determinable by preliminary testing or otherwise, and thus often must be arrived at in multiple surgical procedures. If a greater extent of the venous system is closed, there is an adverse consequence to the patient, and thus some of the implant must be removed. On the other extreme, if the extent of the venous system that is squeezed closed does not obviate the venous leakage necessary to maintain an erection, the patient must undergo additional surgery to receive an additional implant.

In sharp contrast to the prior art procedure, as above generally described, the within inventive method also contemplates the use of implants, but with the significant difference that after being surgically implanted in the patient's penis the same can be varied in size by fluid introduced thereinto or removed therefrom, so that the implants squeeze closed a precisely controled extent of the same veins or venous outflow system that the prior art implants closed and, in this manner, are more effective to obviate venous leakage. That is, and as will be described subsequently in greater detail, an initial selected size of the implants is arranged to squeeze closed an extent of the outflowing venous system, and if in the patient it has an observed effect of not totally obviating venous leakage and curing the impotence, it is a simple matter by a transcutaneous hypodermic procedure to increase the implant size and squeeze more of the venous system veins closed. Similarly, if too great an extent of the venous system is squeezed closed by the implants, their size is readily reduced by removing fluid therefrom.

With the above general understanding of the within inventive method and how it significantly differs from the noted prior art method, reference should be made to FIGS. 1, 2, 3 and 4 which are here used to describe the pertinent physiology of the penis 10.

Figure 2:
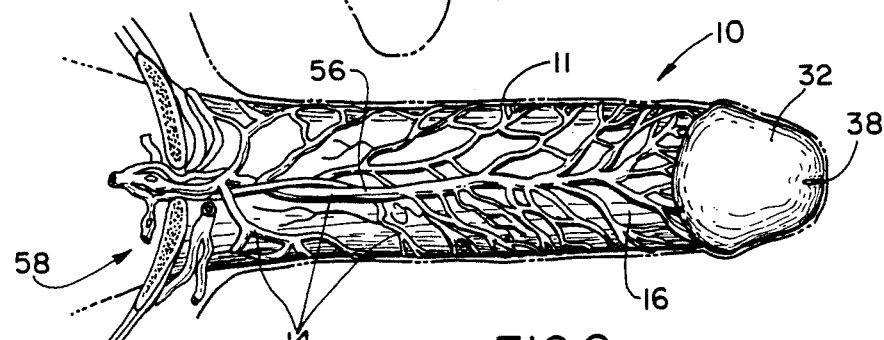
FIG. 2 is a plan view of the penis shown in FIG. 1 illustrating additional parts of the venous or arterial system.
Figure 4:
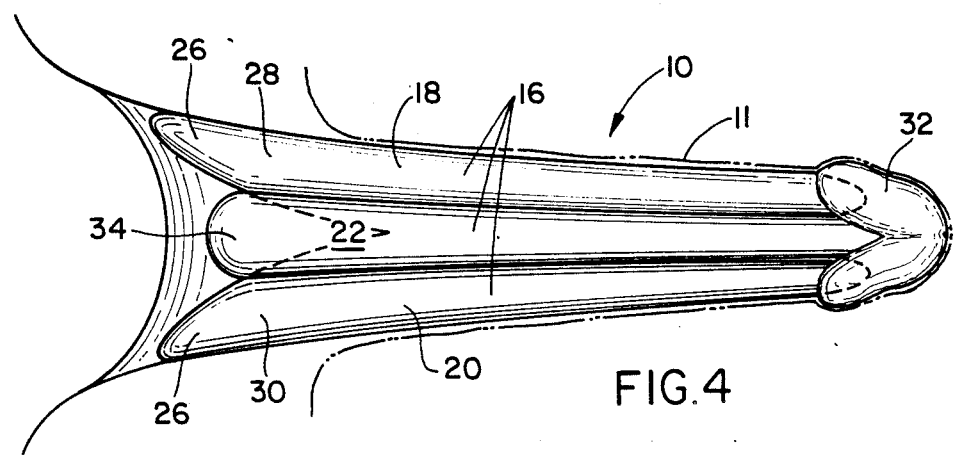
FIG. 4 is a bottom view of the penis shown in FIGS. 1 and 2, which has been simplified by the omission of the blood vessels of the venous system.
Figure 3:
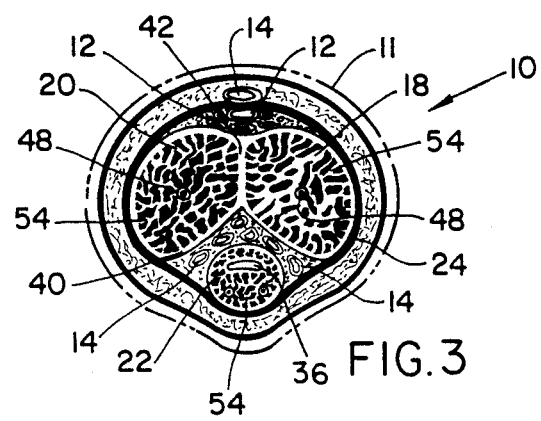
FIG. 3 is a cross section, taken along 3—3 of FIG. 1 but which is common also to FIGS. 2 and 4 and is drawn to a larger scale, which provides further anatomical details.

In FIG. 1 is shown a side elevation of an erect penis 10 with the enveloping skin 11 (integument) shown in phantom line. As already noted, the triple dot line 44 is used to show the profile of the flaccid penis for comparison. In FIG. 1, for simplicity only the parts of the main (pudis) arterial system and some branches are shown, it being understood that the system is comprised of an extensive net work of veins and the like. FIG. 2 shows the same erect penis 10 in plan view with only some main veins 14 and their branches shown. FIG. 3 is a cross section common to FIGS. 1, 2 and 4.

As understood, the penis is mainly comprised of three parallel cylinders 16. The two main cylinders 18 and 20 that form the major part of the erect penis 10 are the corpora cavernosa. The anterior three fourths of these two cylinders 18 and 20 along with the third cylinder 22 of erectile tissue are bound together within the deep fascia 24 (Bucks Fascia) of the penis 10 to enclose the body of the organ in a strong capsule. Towards their posterior end, the corpora cavernosa 18, 20 diverge from each other and terminate as tapering structures called the crura 26, singularly known as the crus 28, 30. (See FIG. 4). The crura 26 are strongly anchored to the pelvic bone (ischium) and are surrounded by muscle. The anterior ends of the corpora cavernosa 18, 20 are securely attached within the "head" of the penis technically known as the glans penis 32. The glans penis 32 is the anterior portion of the corpus spongiosum 22. Between its ends the main portion of the corpus spongiosum 22 is uniform in size but somewhat smaller across than a corpus cavarnosum. The posterior of the corpus spongiosum 22 tapers outwardly to a bulb end 34 where it is securely held between the crura 26. The urethrae 36 enters the bulb 34, 1 or 2 cm. from the posterior end on the dorsal surface and extends the length of the corpus spongiosum 22 terminating in opening 38 at the crown of the glans penis 32.

As seen most clearly in FIG. 3, the corpus cavernosa 18, 20 are enclosed and joined within the second fibrous envelope tunica albuginea 40, the common median wall 42 being the septum.

When the penis 10 is in flaccid condition 44 (FIG. 1) a minimal amount of blood flow takes place. On the occasion that erection of penis 10 takes place, as already noted this requires changes within main artery system 12 to allow for an increase of blood to enter the three cylinders 16 of penis 10 (FIG. 4) through its many branches. The upper branch 46 divides into two deep arteries 48 and into the dorsal branch 50 to supply the incoming blood to the corpora cavernosa 18, 20, while another branch 52 supplies blood to the corpus spongiosum 22. Branches 46 through 52 and their sub branches penetrate the fibrous sheath 24 and supply blood to the three cylinders 16 of penis 10. Contained within cylinders 16 are flexible spongelike structures of cavernous spaces and capillaries 54. In the beginning of an erection, more blood is allowed to flow into penis 10 than is allowed to leave via venous system 14. Thus the penis increases in length and volume. The blood from the cavernous spaces 18, 20, 22 and 32 leaves through a multitude of veins 14 that for the most part join into the deep dorsal vein 56 which runs along the shallow groove above septum 42. However, a greater number of veins 58 known as the veins of the roots in the vicinity of crura 28, 30 carry a considerable amount of blood away from penis 10 towards the prostatic plexus. For the duration of the erection there is a delicate balance of blood flow into and out of the penis 10, controlled by valves within and muscles surrounding arteries 12 and veins 14, resulting in the necessary differential blood pressure to maintain the erection.

In the case of pure venous impotence, the patient is found to have a difficiency in his ability to restrict the outflow of blood from the penis, which as prevously noted is classified as "venous leakage".

As is already known from descrptions in the scientific literature, of which the published results of the doctors M. Degni and R. E. Tullii are exemplany and typical of surgical techniques used on sixty patients with pure venous impotence, it has been possible to correct this type impotence problem by suturing a bundle 59 of three silastic tubes within crura 26 of patients to restrict the outflow of blood through the deep vein and veins of the roots 14. (See FIGS. 5 and 6). However, a significant shortcoming is that the size of the bundle 59, and thus the number of veins and the blood flow therethrough which is necessary to correct the problem, cannot be precisely determined beforehand, and thus adjustments are only possible by removing or adding tubes to change the size of bundle 59.

Figure 8:
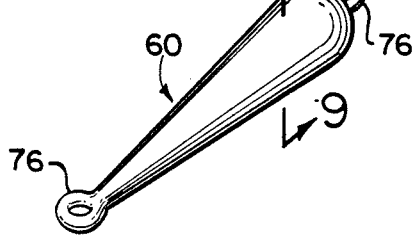
FIG. 8 is an isolated perspective view of the implant device of the present invention before installation.
Figure 9:
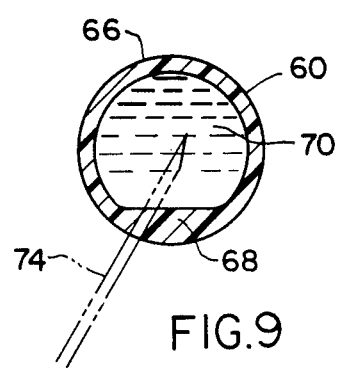
FIG. 9 is a cross section taken along line 9—9 of FIG. 8, showing further structural details.

In sharp contract to the aforesaid, the present invention involves the invagination of two implant devices 60 in the stratagically selected site of the crura 26 of the patient to restrict outflow of blood from the penis 10 during erection which can be size-adjusted post-surgically. That is, the devices 60, which are indentically constructed in a carrot shape as best illustrated in FIG. 8, are to be installed relative to penis 10 in their preferred implant sites and each in an orientation in which the front end 62 is shown to the right with the rear part 64 to the left of FIG. 7. Each carrot shaped device 60 is preferably made of elastic, biocompatible plastic, and is three to four cm. in length with a maximum diameter of 0.4 cm. to conform generally with the typical shape of the crus 26. As seen in FIG. 9, the device 60 is hollow and has a uniform wall 66 throughout, except for a thinckened portion 68 at the major diameter. Portion 68 is oriented towards the patient's perineum 72 to be available for transcutaneous puncture by hypodermic needle 74 after surgical installation. The void within device 60 is filled with fluid 70, preferably distilled water. The plastic of which device 60 is made will be understood to have a self-seal characteristic, such as that used for blood vessel replacement, so that the puncture opening therein seals after needle 74 is removed. By injecting or removing fluid 70, the device 60 can be made larger (up to 1 cm. diameter) of smaller in diameter. On each end 62 and 64, a preferred embodiment of the device 60 is provided with an anchor ring 76.

Figure 7:
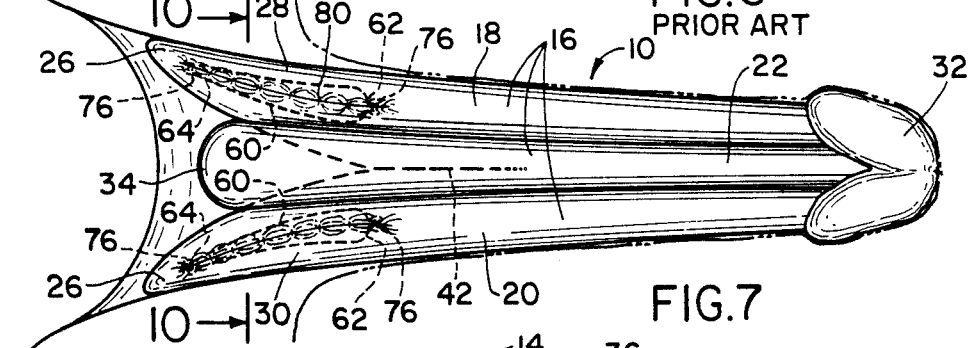
FIG. 7 is again a bottom view similar to FIG. 4, but illustrating the practice of the present inventive method resulting in implants invaginated within the crura.
Figure 10:
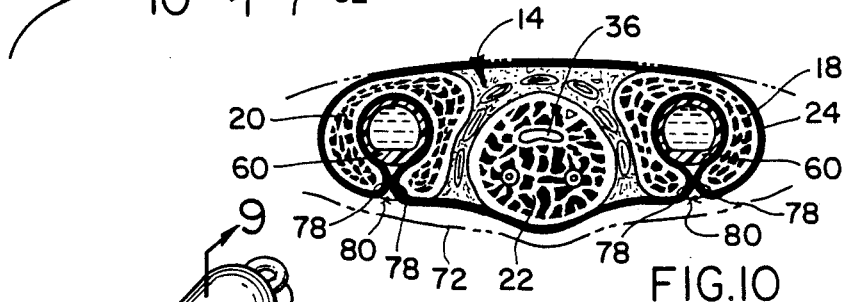
FIG. 10 is a cross section taken along line 10—10 of FIG. 7, illustrating the blood-restricting function of the implants.

As best seen in FIGS. 7 and 10, at installation the device 60 is laid parallel to the surgically exposed crus 26 of the patient and sutured in place by drawing the tough covering 78 of the crus across and about the device 60 with sutures 80. Further suturing 80 of rings 76 insures against linear movement of device 60. A second device 60 is installed in the other crus 26 in like manner. FIG. 10 ilustrates how compression of veins 14 of the roots in the vicinity of crus 26 brings about the desired restriction of blood flow from penis 10. That is, the selected implant site for the devices 60 is one in which each is in a clearance position from the corpus spongiosum with the outflowing venous system through which excess outflowing blood contributing to the patient's venous leakage located in the clearance established by the selection of the implant site. Thereafter by increasing and decreasing the size of each said plastic implant 60, by injecting thereinto and removing therefrom fluid to obtain a fluid volume effective to correspondingly adjust the size of said clearance, the result achieved on the venous system in a decreased clearance is that the network of veins thereof are squeezed closed to the extent effective to counteract the venous leakage.

Thus, after a healing period and performance checks, the present invention contemplates that the patient will confer with the physician for possible size adjustment of devices 60, and if adjustment is necessary that it will be made using the hypodermic needle 74 as already described, and thus avoiding additional surgery which characterizes current surgical techniques for correcting venous leakage impotence.

While the particular surgical procedure or method herein shown and disclosed in detail is fully capable of attaining the objects and providing the advantages hereinbefore stated, it is to be understood that it is merely illustrative of the presently preferred embodiment of the invention and that no limitations are intended other than as defined in the appended claims.

What is claimed is:

1. A method of obviating male impotence due to venous leakage preventing erection of the penis by using hollow plastic implants, said method comprising the steps of selecting two implant sites in which each site is a location in each posterior end of the penis corpora cavernosa adjacent to the penis outflowing venous system and is oriented lengthwise of the penis on opposite sides of the penis centrally located corpus spongiosum, suturing in place each said ;hollow plastic implant at each said selected site in a clearance position from said corpus spongiosum with said outflowing venous system contributing to said venous leakage in said clearance therebetween, and increasing and decreasing the size of each said plastic implant by injecting thereinto and removing therefrom fluid to obtain a fluid volume effective to correspondingly adjust the size of said clearance, whereby said venous system is squeezed closed during erection by said implants creating a reduced clearance therebetween to the extent effective to counteract said venous leakage.

2. The method of obviating male impotence due to venous leakage as claimed in claim 1 wherein each said hollow plastic implant is carrot shaped.

3. The method of obviating male impotence due to venous leakage as claimed in claim 2 wherein the fluid injected into each said hollow plastic implant is distilled water.

4. The method of obviating male impotence due to venous leakage as claimed in claim 3 wherein the injection of the distilled water into each said hollow plastic implant is made using a hypodermic needle.

* * * * *